US009675080B2

(12) United States Patent
Grech (10) Patent No.: US 9,675,080 B2
(45) Date of Patent: Jun. 13, 2017

(54) METHODS FOR DELAYING MATURITY OF CROPS

(75) Inventor: Nigel M Grech, Fresno, CA (US)

(73) Assignee: VERDESIAN LIFE SCIENCES U.S., LLC, Cary, NC (US)

( * ) Notice: Subject to any disclaimer, the term of this patent is extended or adjusted under 35 U.S.C. 154(b) by 601 days.

(21) Appl. No.: 12/718,881

(22) Filed: Mar. 5, 2010

(65) Prior Publication Data

US 2010/0240534 A1    Sep. 23, 2010

Related U.S. Application Data

(60) Provisional application No. 61/162,095, filed on Mar. 20, 2009.

(51) Int. Cl.
| | | |
|---|---|---|
| A01N 59/26 | (2006.01) | |
| A01N 3/00 | (2006.01) | |
| A23B 7/10 | (2006.01) | |
| A23B 7/154 | (2006.01) | |
| A01N 43/08 | (2006.01) | |

(52) U.S. Cl.
CPC ............ *A01N 59/26* (2013.01); *A01N 3/00* (2013.01); *A01N 43/08* (2013.01); *A23B 7/10* (2013.01); *A23B 7/154* (2013.01)

(58) Field of Classification Search
CPC .................................................... A01N 59/06
See application file for complete search history.

(56) References Cited

U.S. PATENT DOCUMENTS

| | | | |
|---|---|---|---|
| 1,704,456 A | 3/1929 | Barger | |
| 1,943,468 A | 1/1934 | Bridgeman et al. | |
| 2,379,294 A | 6/1945 | Gooding | |
| 2,443,795 A | 6/1948 | MacRill et al. | |
| 2,460,710 A | 2/1949 | Nolan | |
| 2,489,744 A | 11/1949 | Brogden | |
| 2,920,996 A | 1/1960 | Bluestone | |
| 3,139,347 A | 6/1964 | Sair et al. | |
| 3,189,467 A | 6/1965 | Kalmar | |
| 3,231,392 A | 1/1966 | Sair | |
| 3,370,957 A | 2/1968 | Wagner et al. | |
| 3,410,696 A | 11/1968 | Rosenfield | |
| 3,420,790 A | 1/1969 | Gassner | |
| 3,658,813 A | 4/1972 | Godefroi et al. | |
| 3,759,719 A | 9/1973 | Hodel et al. | |
| 3,888,984 A | 6/1975 | Hughes | |
| 4,006,259 A | 2/1977 | Kalmar | |
| 4,075,324 A | 2/1978 | Thizy et al. | |
| 4,434,185 A | 2/1984 | Nelson | |
| 4,614,659 A * | 9/1986 | Liu ............................. | 426/321 |
| 4,917,820 A | 4/1990 | Matsumoto et al. | |
| 5,500,403 A | 3/1996 | Shafer et al. | |
| 5,514,200 A | 5/1996 | Lovatt | |
| 5,707,418 A * | 1/1998 | Hsu ............................. | 71/32 |
| 5,736,164 A | 4/1998 | Taylor | |
| 5,800,837 A | 9/1998 | Taylor | |
| 5,830,255 A | 11/1998 | Lovatt | |
| 5,865,870 A | 2/1999 | Hsu | |
| 5,922,649 A | 7/1999 | Pehu et al. | |
| 5,997,910 A | 12/1999 | Taylor | |
| 6,083,876 A | 7/2000 | Jokinen et al. | |
| 6,113,665 A | 9/2000 | Lovatt | |
| 6,114,285 A * | 9/2000 | Padilla et al. ................ | 504/184 |
| 6,139,879 A | 10/2000 | Taylor | |
| 6,168,643 B1 | 1/2001 | Hsu | |
| 6,228,885 B1 | 5/2001 | Palla et al. | |
| 6,338,860 B1 | 1/2002 | Taylor | |
| 6,509,041 B2 | 1/2003 | Taylor | |
| 6,645,268 B2 | 11/2003 | Lovatt | |
| 6,896,714 B2 | 5/2005 | Lovatt | |
| 6,929,673 B1 | 8/2005 | Lovatt | |
| 7,160,349 B2 | 1/2007 | Lovatt | |
| 7,160,350 B2 | 1/2007 | Lovatt | |
| 7,345,008 B1 | 3/2008 | Suzuki et al. | |
| 1,900,295 A1 | 3/2009 | Ore | |
| RE41,789 E | 10/2010 | Lovatt | |
| RE43,073 E | 1/2012 | Lovatt | |
| 2003/0087014 A1 | 5/2003 | Kemp et al. | |
| 2006/0084573 A1 * | 4/2006 | Grech et al. .................. | 504/101 |
| 2006/0283223 A1 * | 12/2006 | Grech ..................... | A01N 47/14 71/31 |
| 2007/0142227 A1 | 6/2007 | Rajamannan | |
| 2008/0014306 A1 | 1/2008 | Castro | |
| 2008/0145499 A1 | 6/2008 | Sardo | |
| 2008/0248128 A1 | 10/2008 | Sardo | |
| 2009/0095040 A1 | 4/2009 | Dean | |
| 2009/0227455 A1 | 9/2009 | Grech | |

FOREIGN PATENT DOCUMENTS

| | | |
|---|---|---|
| CA | 2644188 | 8/2008 |
| DE | 23 44 887 A1 | 3/1975 |

(Continued)

OTHER PUBLICATIONS

Clua et al. (Increase in forage yield in narrowleaf birdsfoot trefoil in permanent pasture with foliar applied gibberellic acid and phosphorus, Plant Growth Regulation 21; p. 223-228, 1997.*

(Continued)

*Primary Examiner* — Ali Soroush
*Assistant Examiner* — Danielle Sullivan
(74) *Attorney, Agent, or Firm* — Alston & Bird LLP (57) ABSTRACT

Methods for delaying the maturity, coloration and/or senescence of fruits, vegetables, ornamentals, or non-food crops by applying phosphorous acid and/or its salts to the plants; or by applying mixtures of gibberellic acid and/or its salts and phosphorous acid and/or its salts to the plants. Applications may be made pre- or post-harvest at various temperatures and pH ranges. The unique combinations of phosphorous acid/salts with gibberellic acid/salts in embodiments of the present invention have been found to increase the effect of the gibberellic acid/salts on delaying maturation, coloration and senescence of plant tissues, thereby prolonging the shelf life of fruit, vegetables and/or non food crops in ways not previously realized.

32 Claims, 4 Drawing Sheets

(56) References Cited

FOREIGN PATENT DOCUMENTS

| | | |
|---|---|---|
| DE | 197 10 127 A1 | 9/1998 |
| EP | 336489 | 10/1989 |
| EP | 1941802 A1 | 9/2008 |
| ES | 2078180 A1 | 12/1995 |
| ES | 2303808 | 8/2008 |
| JP | 64 010943 | 1/1989 |
| WO | 99-12422 | 3/1999 |
| WO | 00/16644 A1 | 3/2000 |
| WO | 03-011030 | 2/2003 |
| WO | 2005-074684 | 8/2005 |
| WO | 2007-017409 | 2/2007 |
| WO | 2007/101495 A | 9/2007 |
| WO | 2007-101848 | 9/2007 |
| WO | 2007-128743 | 11/2007 |
| WO | 2008000741 | 1/2008 |
| WO | 2008-034785 | 3/2008 |

OTHER PUBLICATIONS

Tomlin, C. "The e-pesticide manual 1999-2000, gibberellic acid (379) The Bio Pesticide Manual 1:07, Plant Growth Regulator" Electronic Pesticide Manual, British Crop Protection Council, GB, No. 379, Jan. 1, 1999 (Jan. 1, 1999), pp. 1-2, XP002253914.

Tomlin, C. "661 phosphonic acid" The E-Pesticide Manual: A World Compendum, Alton: British Crop Protection Council, GB, Jul. 1, 2006 (Jul. 1, 2006), p. 661, XP002537979.

Garcia-Luis, A; Augusti M; Amela V; Romoero, E; Guardiola, J L: "Effect of Gibberellic Acid on Ripening and Peel Puffing in 'Satsuma' Mandarin", Scientia Horticulturae, vol. 27, 1985, pp. 75-86, XP007914752, ISSN: 0304-4238.

Gross, J; Bazak, H; Blumenfeld, A; Ben-Arie, R: "Changes in Chlorophyll and carotenoid pigments in the peel of 'triumph' persimmon (diospyros kaki 1.) induced by pre-harvest gibberellin (GA3) treatment", Scientia Horticulturae, vol. 24, 1984, pp. 305-314, XP007914759, ISSN: 0304-4238.

EPO Search Report: EP 10 25 0514, Sep. 13, 2010.

Wills, R., et al. "Postharvest an Introduction to the Physiology & Handling of Fruit, Vegetables and Ornamentals" University of New South Wales Press Ltd., Chapter 9, pp. 144-158 (4th Ed. 1998).

Igoe, R. "Dictionary of Food Ingredients" Van Nostrand Reinhold, New York, pp. 28-29, 102-103, 108-109, and 128-129 (1989).

Kader, A. "Postharvest Technology of Horticultural Crops" University of California Agriculture and Natural Resources Publication 3311, Chapter 17, pp. 163-195, (Third Ed. 2002).

Journal of Bacteriology, Influence of Sorbic Acid on the Growth of Certain Species of Bacteria, Yeasts, and Filamentous Fungi, 771 pp. 573-580, 1959, Bell, et al.

Food Technology, vol. 59, No. 2, pp. 124-128, Feb. 2005.

The Commercial Storage of Fruits, Vegetables, and Florist and Nursery Stocks, USDA Handbook No. 66, Sep. 1954, Wright, et al.

John N. Sofos: "Interactions and Synergistic Effects"; Sorbate Food Preservatives, Jan. 1, 1989 (Jan. 1, 1989), pp. 55-94, XP009120020, ISGN: 0-8493-6786-7 (p. 72 paragraphs 2 through 5 and p. 75, paragraphs 2 through 5).

Tomlin C D S: "661 Phosphonic acid", The E-Pesticide Manual, a World Compendium, Jul. 2006 (Jul. 2007), XP002537979, ISGN: 1 901396 42 8; Section "Products".

Brown, G.E., Plant Disease, vol. 68, No. 5, pp. 415-417. 1984.

Chastagner, et al., Phytopathology (USA), Jan. 1979.

Smilanick, et al., Plant Disease, Am. Phytopath. Society, 1997.

Sugar, et al., Management of Nitrogen and Calcium in Pear Trees for Enhancement of Fruit Resistance to Postharvest Decay; Hort-Technology, vol. 2(3), Jul.-Sep. 1992, pp. 382-387, Published by American Society for Hortcultural Science, Alexandria, VA.

European Search Report, Aug. 7, 2009.

Aharoni, Y. Fungicide application in water and in wax for decay control in "Galia" melons. New Zealand Journal of Crop and Horticultural Science, vol. 20, No. 2, pp. 177-179 (1992).

* cited by examiner

Navel Oranges

Fig. 1

Lemons

METHODS FOR DELAYING MATURITY OF CROPS

This application claims the benefit of U.S. Provisional application No. 61/162,095 filed on Mar. 20, 2009, which is incorporated herein by this reference in its entirety.

BACKGROUND OF THE INVENTION

This invention relates to delaying harvests of fruit, vegetables or non food crops. In particular, the present invention relates to methods for delaying the harvest and/or maturity and/or prolonging the shelf life of fruit, vegetables or non food crops using applications containing gibberellic acid and/or its salts and phosphorous acid and/or its salts.

FIELD OF THE INVENTION

It is a well known practice in fruit, vegetable and non-food crops to try and optimize and adjust the crop harvest period in order to maximize marketability of the particular crop.

Gibberellic acid is well known in literature to delay the process of produce maturation. However gibberellic acid and/or its salts sprays applied to produce require that the particular produce being sprayed be adequately covered, and that the gibberellic acid have an exposure period on the produce that ensures adequate uptake. Historically, fruit such as citrus can be sprayed (sometimes in situ—pre harvest) with gibberellic acid to delay harvest, but on occasion problems with uptake and efficient product efficacy have been experienced.

Phosphorous acid and/or its salts when applied to plants are well known to metabolically stimulate plants and to provide protections against certain plant pathogens.

With increasing regulatory and environmental pressure being applied to agrochemicals, there is an increasing desire to reduce agrochemical residues on crops and increase the performance of existing materials used on such crops.

SUMMARY OF THE INVENTION

The present invention provides novel methods for improving the crop maturation delaying attributes of gibberellic acid and its salts to reduce physiological decay and/or spoilage of fruits, vegetables and non-food crops. Embodiments of the present invention include materials applied to fruit, vegetables or non-food crops that contain mixtures of gibberellic acid and/or its salts and phosphorous acid and/or its salts. Other embodiments contain mixtures of phosphorous acid and/or its salts, including without limitation, phosphorous acid salts (phosphites) of potassium, sodium, ammonium, and/or calcium.

It is known that gibberellic acid (and/or its salts) have an effect on delaying maturation and/or senescence of plant tissues. Many of the novel compositions of the present invention combine gibberellic acid (and/or its salts) with phosphorous acid (and/or its salts) in unique compositions which cause the effect of the gibberellic acid/salts) to be much more pronounced. The phosphorous acid/salts provide a unique synergistic effect with the gibberellic acid/salts in these compositions. The unique combinations of phosphorous acid/salts with gibberellic acid/salts in these compositions increase the effect of the gibberellic acid/salts on delaying maturation, coloration and senescence of plant tissues, thereby prolonging the shelf life of fruit, vegetables and/or non food crops in ways not previously realized.

DETAILED DESCRIPTION

The invention is further illustrated by the following non-limiting examples. It is to be appreciated that, although each of the exemplary experiments used potassium phosphite, that other salts of phosphorous acid, including without limitation, ammonium, sodium, and/or calcium salts, as well as phosphorous acid itself may also have been used. For examples 1 and 2 below, assessment of citrus fruit peel color was made using the following color grading charts (FIG. 1 for Navels; FIG. 2 for Lemons) in addition to the *Dictionary of Color* by Maerz and Paul, First Edition (1930). All experiments were conducted in solutions at approximately pH 6, although pH ranges from between about 3 and about 9 are acceptable.

Table 1 below sets forth approximate cross-references to the *Dictionary of Color* for the eight colors of FIG. 1:

TABLE 1

| |
|---|
| 1: 10-L-7 |
| 2: 9-L-5 |
| 3: 9-L-2 |
| 4: 10-L-1 |
| 5: 11-L-1 |
| 6: 19-L-2 |
| 7: 20-L-5 |
| 8: 21-L-5 |

Table 2 below sets forth approximate cross-references to the *Dictionary of Color* for the eight colors of FIG. 2:

TABLE 2

| |
|---|
| 1: 10-L-5 |
| 2: 10-L-4 |
| 3: 10-L-2 |
| 4: 10-L-4 |
| 5: 11-K-3 |
| 6: 12-L-2 |
| 7: 13-K-3 |
| 8: 13-L-5 |

EXAMPLE 1

Five different treatments (A-E below) were made. There were four replications for each of the five treatments, with each replicate comprising six fruit pieces. Thus, each treatment was applied to 24 fruit pieces. The fruit treated in this example were green lemons (initial color between stage 5 and 6 (approx 5.5) at the color break stage. Possible immersion temperatures can be between approximately 45° F. (7° C.) and 150° F. (66° C.), with an ideal temperature of 50° F. (10° C.) which was used in the trials below.

Each treatment was as follows:

A. The fruit was immersed in untreated water.

B. The fruit was immersed in a solution of gibberellic acid (100 ppm) in water for 2 minutes.

C. The fruit was immersed in a water solution containing 2% (w/w) potassium phosphite for 2 minutes.

D. The fruit was immersed for 2 minutes in a water solution containing a mixture of 2% (w/w) potassium phosphite and gibberellic acid (100 ppm)

E. The fruit was immersed for 2 minutes in a mixture of gibberellic acid (100 ppm) and a 3% (w/w) potassium phosphite solution.

After the treatments were applied and left to dry for 10 minutes, all treatments were recorded for peel color using FIG. 2 above and the *Dictionary of Color*, and rated for color development and photographed. The fruit was placed in humid incubators at 15° C. and monitored weekly for color development.

EXAMPLE 2

Five different treatments (A-E below) were made. There were four replications for each of the five treatments, with each replicate comprising six fruit pieces. Thus, each treatment was applied to 24 fruit pieces. The fruit treated in this example were oranges at the color break stage, the fruit being predominantly green with some development of orange color (initial color 5.5). Possible immersion temperatures can be between approximately 45° F. (7° C.) and 150° F. (66° C.), with an ideal temperature of 50° F. (10° C.) which was used in the trials below.

Each treatment was as follows:

A. The fruit was immersed in untreated water.

B. The fruit was immersed in a solution of gibberellic acid (100 ppm) in water for 2 minutes.

C. The fruit was immersed in a water solution containing 2% (w/w) potassium phosphite for 2 minutes.

D. The fruit was immersed for 2 minutes in a water solution containing a mixture of 2% (w/w) potassium phosphite and gibberellic acid (100 ppm)

E. The fruit was immersed for 2 minutes in a mixture of gibberellic acid (100 ppm) and a 3% (w/w) potassium phosphite solution.

Figure 1:
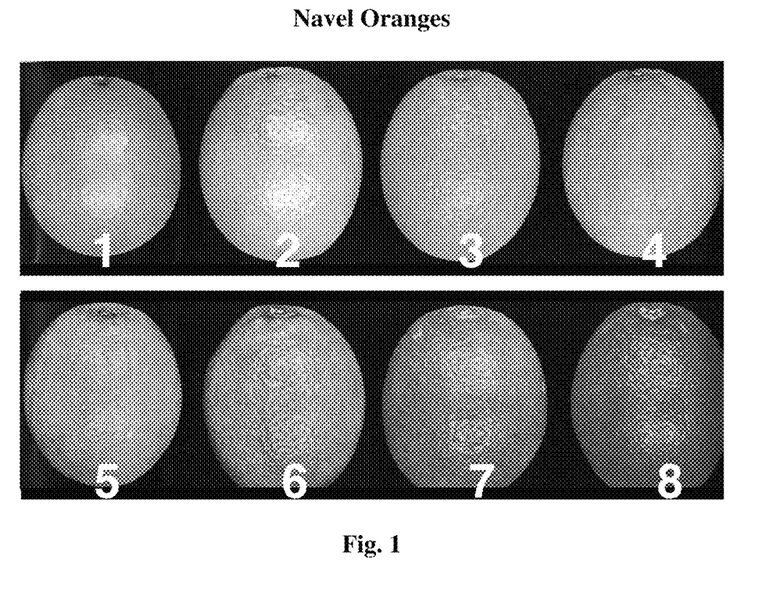
FIG. 1 is a photograph of different colored navel oranges referred to in examples 1 and 2, and table 1.
Figure 2:
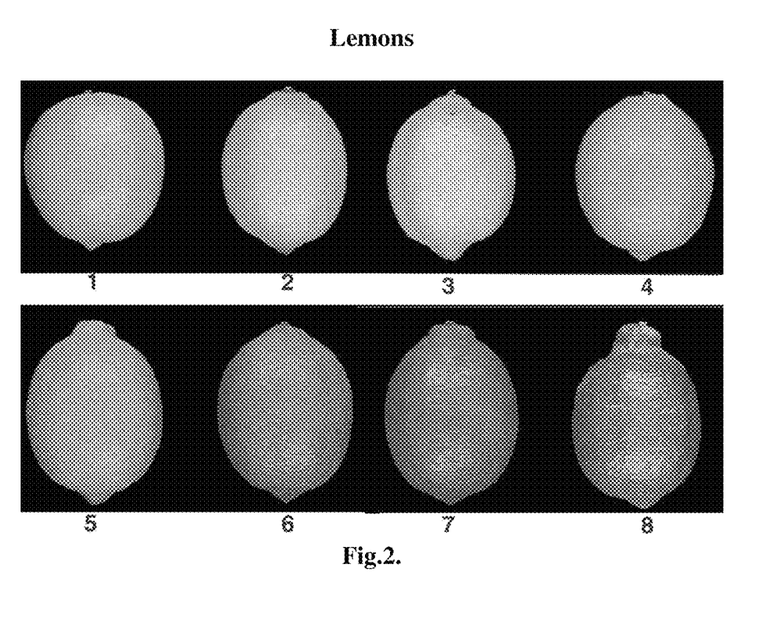
FIG. 2 is a photograph of different colored lemons referred to in examples 1 and 2, and table 2.

After the treatments were applied and left to dry for 10 minutes, all treatments were recorded for peel color using FIG. 1 above and the *Dictionary of Color*, and rated for color development and photographed. The fruit was placed in humid incubators at 15° C. and monitored weekly for color development.

Table 3 below sets forth results of fruit dipping examples 1 and 2, with color references to the charts of FIGS. 1 and 2. Treatments followed by the same letter in each row are not significantly different at p=0.05 according to the Student Neuman-Keuls test at a probability level of P=0.05.

TABLE 3

Mean Color Rating

| | A. Control | B. Gibberellic acid (GA) 100 ppm | C. Phosphite | D. Phosphite (2%) + GA 100 ppm | E. Phosphite (3%) + GA 100 ppm |
|---|---|---|---|---|---|
| Lemons | 2.1 a | 3 b | 3.6 c | 4 d | 4.75 e |
| Navels | 1.4 a | 3.2 b | 3.5 bc | 3.8 c | 5 d |

Figure 3:
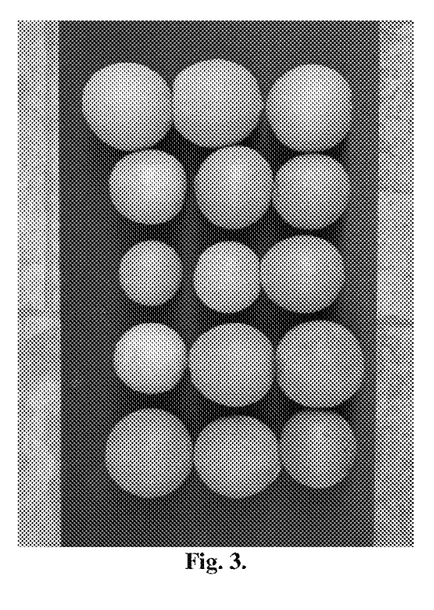
FIG. 3 is a photograph of representative fruit from example 2 after 30 days.

FIG. 3 illustrates representative fruit from example 2 after 30 days in. From top to bottom, the 5 rows of fruit represent the 5 treatments: A (control), B (GA 100 ppm), C (phosphite), D (phosphite 2%+GA 100 ppm) and E (phosphite 3%+GA 100 ppm).

Table 4 below sets forth approximate colors from the *Dictionary of Color* corresponding to the five rows of fruit of FIG. 3:

TABLE 4

| A: | 9-L-5 | 9-L-6 | 9-L-5 |
| B: | 9-L-4 | 10-L-1 | 9-L-4 |
| C: | 9-L-2 | 9-L-1 | 9-L-5 |
| D: | 9-L-4 | 10-K-3 | 9-K-2 |
| E: | 9-L-1 | 9-L-1 | 20-L-1 |

EXAMPLE 3

Five different treatments (T1-T5 below) were made. There were four replications for each of the five treatments, with each replicate comprising one navel orange tree (variety Cara Cara) in situ. Thus, each treatment was applied to 4 different trees. Treatments were all made using a motorized high volume agricultural sprayer and an application volume equivalent to 5000 L/ha (liters/hectare), or approximately 530 gallons/acre. This is approximately equivalent to 12.5 L (3.3 gal)/tree. The trees were sprayed during early color break (late October/early November) with a wetting agent added at 0.01% (v/v).

Treatments were as follows:

T1. Untreated trees=control.

T2. Water solution containing gibberellic acid at 16 ppm.

T3. Water solution containing potassium phosphite (expressed as equivalent amount of phosphorous acid) sprayed at 600 ppm.

T4. A tank water mixture of potassium phosphite (expressed as equivalent amount of phosphorous acid) sprayed at 300 ppm plus gibberellic acid at 16 ppm T5. A tank water mixture of potassium phosphite sprayed at 600 ppm plus gibberellic acid at 16 ppm The spray tank pH for all the treatments T2-T5 were adjusted with citric acid to a pH of between about 5 and about 6 (in accordance with the manufacturers instructions for gibberellic acid usage), and a small amount of a non ionic wetter added to the tank (0.01% v/v). At the time of application, field temperatures varied between about 0-10° C. (night) [32-50° F.] and about 10-25° C. (day) [50-77° F.]. The fruit on the trees were assessed for color development approximately 30 days later, during December. Table 5 below sets forth results of field trial example 4 on the fruit of the subject trees with color references to the chart of FIG. 1. Treatments followed by the same letter in each row are not significantly different at p=0.05 according to the Student Neuman-Keuls test at a probability level of P=0.05. The above temperature ranges reflect the ambient high and low temperatures in central California during the late fall season, prior to citrus harvest.

It is to be appreciated that for application to crops harvested in the spring or summer, the ambient temperature may range between about 20° C. and 30° C. (68-86° F.) in mild conditions, and as low as about 10° C. (50° F.) to as high as about 37° C. (99° F.). It is not recommended that the materials of the present invention be applied at temperatures much higher than about 30° C. (86° F.), with the preferred temperature range being between about 10° C. and about 30° C.

TABLE 5

| | Mean Color Rating | | | |
|---|---|---|---|---|
| T1. Control | T2. Gibberellic acid (GA) 16 ppm | T3. Phosphite 600 ppm | T4. Phosphite 300 ppm + GA 16 ppm | T5. Phosphite 600 ppm + GA 16 ppm |
| Navels 1.4 a | 3.2 b | 3.5 bc | 3.8 c | 5 d |

Figure 4:
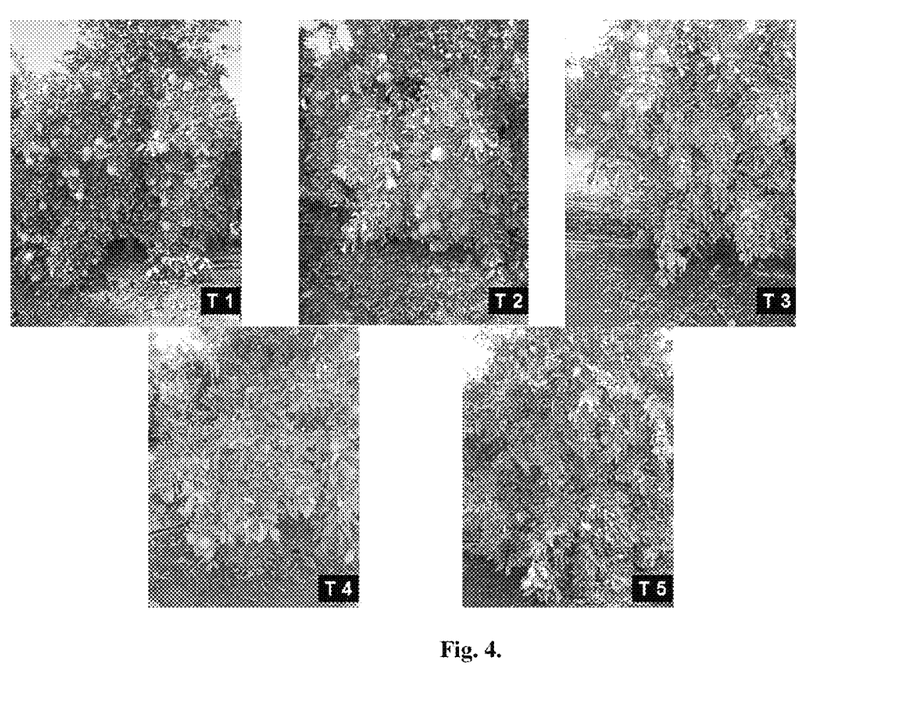
FIG. 4 is a photograph of representative field treatment trees from example 3.

FIG. 4 sets forth representative field treatment trees from example 3.

EXAMPLE 4

For example 4 below, assessment of the tomato peel color was made using the USDA color grading chart (FIG. 5) in addition to the *Dictionary of Color*.

The color grading chart (FIG. 5) is a reproduction of the "Tomato Color Standards USDA Visual Aid TM-L-1" which consists of a chart containing twelve color photographs illustrating certain color classification requirements. The official USDA chart is incorporated herein by this reference. Table 6 below sets forth approximate cross-references to the *Dictionary of Color* for the 12 colors of the USDA chart:

TABLE 6

Figure 5:
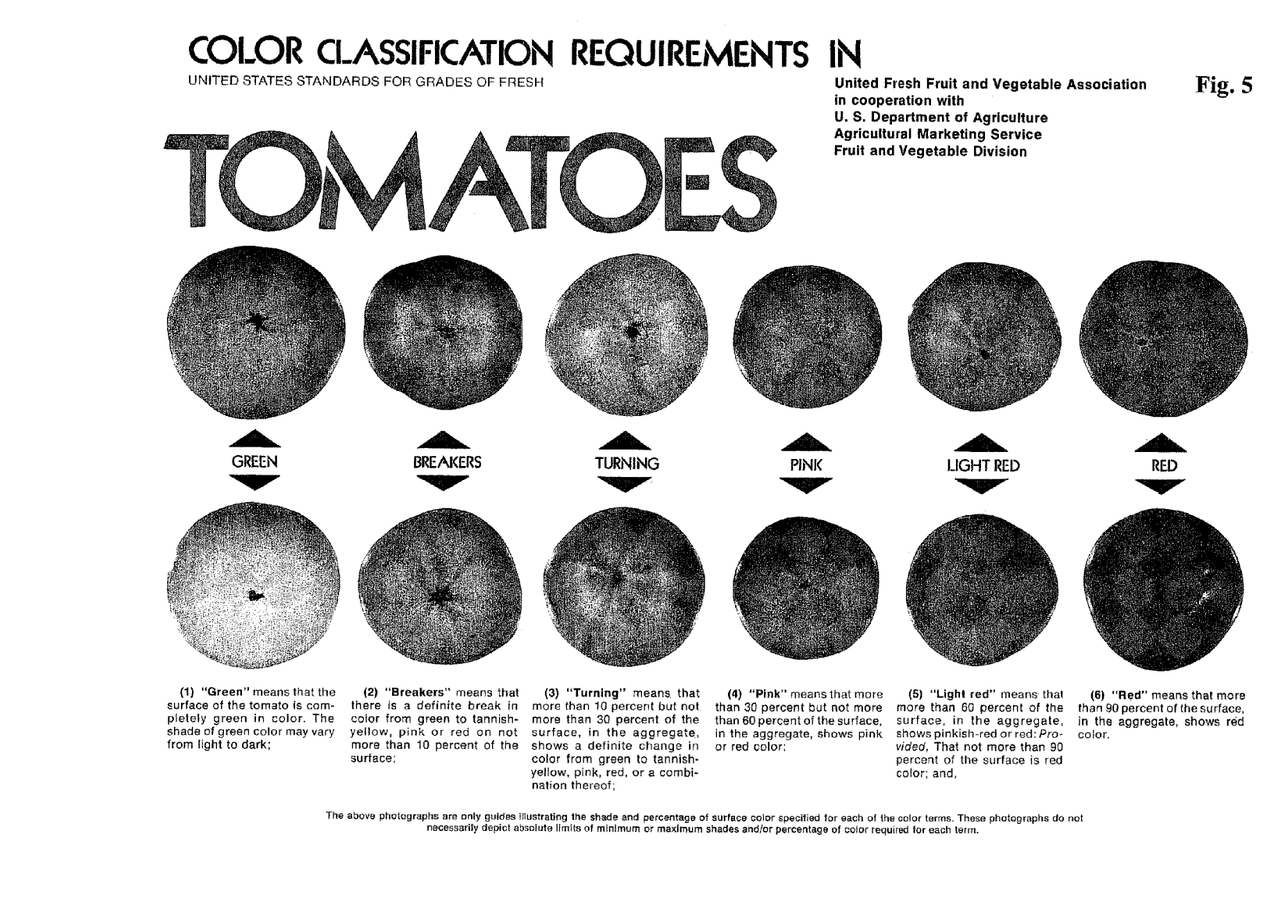
FIG. 5 is a reproduction of the "Tomato Color Standards USDA Visual Aid TM-L-1" which is a chart of twelve color photographs illustrating certain color classification requirements.

| 13-K-2 | 13-K-6 | 12-L-1 | 11-I-10 | 11-H-1 | 11-L-12 |
|---|---|---|---|---|---|
| 11-L-2 | 12-K-5 | 12-K-6 | 11-I-10 | 2-A-12 | 2-I-12 |

In example 4, five different treatments (A-E below) were made. There were four replications for each of the five treatments, with each replicate comprising six fruit pieces. Thus, each treatment was applied to 24 fruit pieces. The fruit treated in this example were firm green tomatoes according to the chart above was 3.5 (initial color 11-C-22) at the onset of color break. Immersion temperatures were approximately 75° F. (24° C.).

Treatments were as follows:
A. The fruit was immersed in untreated water.
B. The fruit was immersed in a solution of gibberellic acid (100 ppm) in water for 2 minutes.
C. The fruit was immersed in a water solution containing 2% (w/w) potassium phosphite for 2 minutes.
D. The fruit was immersed for 2 minutes in a water solution containing a mixture of 2% (w/w) potassium phosphite and gibberellic acid (100 ppm)
E. The fruit was immersed for 2 minutes in a mixture of gibberellic acid (100 ppm) and a 3% (w/w) potassium phosphite solution.

After the treatments were applied and left to dry for 10 minutes, all treatments were recorded for peel color using the *Dictionary of Color* and also the USDA Tomato Color Standards Chart (FIG. 5 herein), and rated for color development and photographed. The fruit was placed in humid incubators at 30° C. (86° F.) and monitored weekly for color development.

This experiment (example 4) was repeated twice.

Table 7 below sets forth results of example 5 on the subject tomatoes with color references to the chart of FIG. 5. Treatments followed by the same letter in each row are not significantly different at p=0.05 according to the Student Neuman-Keuls test at a probability level of P=0.05.

TABLE 7

| | Mean Color Rating | | | |
|---|---|---|---|---|
| A. Control | B. Gibberellic acid (GA) 100 ppm | C. Phosphite 2% | D. Phosphite (2%) + GA (100 ppm) | E. Phosphite (3%) + GA 100 ppm |
| Tomatoes 5.8 a | 4.6 b | 4.8 b | 4.6 b | 3.8 c |

Figure 6:
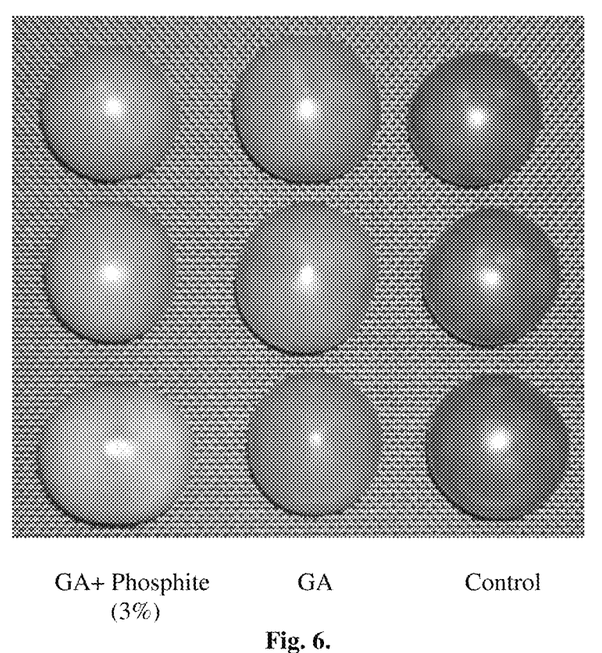
FIG. 6 is a photograph of representative fruit from example 4.

FIG. 6 illustrates representative fruit from example 4. Table 8 sets forth approximate colors from the *Dictionary of Color* corresponding to the three rows of fruit of FIG. 6:

TABLE 8

| 9-L-10 | 9-L-12 | 2-F-12 |
|---|---|---|
| 9-L-9 | 9-L-12 | 2-F-12 |
| 9-L-8 | 9-L-12 | 2-F-12 |

EXAMPLE 5

Five different treatments (A-E below) were made. There were four replications for each of the five treatments, with each replicate comprising ten grape leaves. Thus, each treatment was applied to 40 leaves. The leaves treated in this example were green (initial color 30-L-12). Immersion temperatures were between approximately 75° F. (24° C.).

Treatments were as follows:
A. The leaves were immersed in untreated water.
B. The leaves were immersed in a solution of gibberellic acid (100 ppm) in water for 2 minutes.
C. The leaves were immersed in a water solution containing 2% (w/w) potassium phosphite for 2 minutes.
D. The leaves were immersed for 2 minutes in a water solution containing a mixture of 2% (w/w) potassium phosphite and gibberellic acid (100 ppm)
E. The leaves were immersed for 2 minutes in a mixture of gibberellic acid (100 ppm) and a 3% (w/w) potassium phosphite solution.

After the treatments were applied and left to dry for 10 minutes, all treatments were recorded for color using the *Dictionary of Color*, and rated for color development. Leaves were placed in humid incubators at approximately 25° C. (77° F.) and monitored daily for color development.

This experiment (example 5) was repeated twice.

Results:

| | Mean Color Rating (from Dictionary of Color) | | | |
|---|---|---|---|---|
| A. Control | B. Gibberellic acid (GA) 100 ppm | C. Phosphite 2% | D. Phosphite (2%) + GA (100 ppm) | E. Phosphite (3%) + GA 100 ppm |
| Grape leaves 21-H-9 | 21-F-12 | 21-E-11 | 30-K-11 | 30-K-11 |

SUMMARY

The above experiments show that phosphorous acid/salts (phosphites) alone and gibberellic acid/salts alone each inhibit the maturation and ripening process of plant products such as fruit, vegetables and non food crops. However, the combination of phosphorous acid and/or its salts with gibberellic acid and/or its salts provides highly effective inhibition of maturation and delay in color development. The unique combinations of phosphorous acid/salts with gibberellic acid/salts in embodiments of the present invention increase the effect of the gibberellic acid/salts on delaying maturation and senescence of plant tissues, thereby prolonging the shelf life of fruit, vegetables and/or non food crops in ways not previously realized. Preferred pH ranges are between approximately 4.5 and 6. The maturation delaying effect is more pronounced at higher temperatures.

It is to be appreciated that the term "crop" referred to herein and in the appended claims is to be interpreted broadly to include any harvestable portion of a plant that may be used for commercial purposes, and includes without limitation, fruit, vegetables, leaves, any part of a flower (including without limitation such things as saffron and lavender), stems, roots, shoots, seeds, pods, nuts, bulbs, etc., or any part or portion thereof.

It is to be understood that variations, permutations, combinations and modifications of the present invention may be made without departing from the scope thereof. One or more features of an exemplary embodiment as described above may be practiced in conjunction with other exemplary embodiments as described above. It is also to be understood that the present invention is not to be limited by the specific embodiments or experiments disclosed herein, but only in accordance with the appended claims when read in light of the foregoing specification.

What is claimed is:

1. A method of delaying the maturation of a crop comprising the steps of:
   a. preparing a mixture comprising at least one phosphite source selected from the group consisting of phosphorous acid, a salt of phosphorous acid, and combinations thereof, wherein the total concentration of said at least one phosphite source in said mixture is not greater than about 2% and about 3% (w/w); and a gibberellic acid source selected from the group consisting of gibberellic acid, a salt of gibberellic acid, and combinations thereof wherein said mixture comprises an aqueous solution; and
   b. applying said mixture to exterior surfaces of said crop in order to delay the maturation of said crop.

2. The method of claim 1 where the concentration range of said gibberellic acid source is about 100 ppm.

3. The method of claim 1 wherein said crop is sprayed with the mixture in situ pre harvest.

4. The method of claim 1 wherein the pH of said mixture is between about 3 and about 9.

5. The method of claim 1 wherein the pH of said mixture is about 6.

6. The method of claim 1 wherein said mixture is applied post harvest.

7. The method of claim 1 wherein said mixture is applied at a temperature of between about 45° F. and about 150° F.

8. The method of claim 1 wherein said mixture is applied at a temperature of about 50° F.

9. The method of claim 1 wherein said mixture is applied at a temperature of about 75° F.

10. The method of claim 1 wherein said mixture is applied at an ambient temperature.

11. The method of claim 1 wherein said mixture is sprayed onto crop in a field having night temperatures of between about 0° C. and about 10° C., and day temperatures of between about 10° C. and about 25° C.

12. The method of claim 1 wherein said mixture is sprayed onto crop in a field having an ambient temperature range of between about 10° C. and about 30° C.

13. A method of delaying the maturation of a crop comprising the steps of:
   a. harvesting a crop; and
   b. applying a mixture to exterior surfaces of said harvested crop in order to delay the maturation thereof, said mixture comprising an aqueous solution comprising
      at least one phosphite source selected from the group consisting of phosphorous acid, a salt of phosphorous acid, and combinations thereof, wherein the total concentration of said at least one phosphite source in said mixture is not greater than about 2% and about 3% (w/w), and
      a gibberellic acid source selected from the group consisting of gibberellic acid, a salt of gibberellic acid, and combinations thereof.

14. The method of claim 13 where the concentration range of said gibberellic acid source is about 100 ppm.

15. The method of claim 13 wherein the pH of said mixture is between about 3 and about 9.

16. The method of claim 13 wherein the pH of said mixture is about 6.

17. The method of claim 13 wherein said mixture is applied at a temperature of between about 45° F. and about 150° F.

18. The method of claim 13 wherein said mixture is applied at a temperature of about 50° F.

19. The method of claim 13 wherein said mixture is applied at a temperature of about 75° F.

20. A method of delaying the maturation of harvested crop comprising the step of applying to exterior surfaces said harvested crop a mixture comprising
   at least one phosphite source selected from the group consisting of phosphorous acid, a salt of phosphorous acid, and combinations thereof, wherein the total concentration of all said phosphite sources in said mixture is not greater than about 2% and about 3% (w/w), and
   a gibberellic acid source selected from the group consisting of gibberellic acid, a salt of gibberellic acid, and combinations thereof.

21. A method of delaying the maturation of a crop comprising the steps of:
   a. preparing a mixture comprising at least one phosphite source selected from the group consisting of phosphorous acid, an ammonium salt of phosphorous, a calcium salt of phosphorous acid, a potassium salt of phosphorous acid, a sodium salt of phosphorous acid, and combinations thereof, wherein the total concentration of all phosphite sources in said mixture is not greater than about 2% and about 3% (w/w); and a gibberellic acid source selected from the group consisting of gibberellic acid, a salt of gibberellic acid, and combinations thereof wherein said mixture comprises an aqueous solution; and
   b. applying said mixture to exterior surfaces of said crop in order to delay the maturation of said crop.

22. The method of claim 21 wherein said crop is sprayed with the mixture in situ pre harvest.

23. The method of claim 21 wherein the pH of said mixture is between about 3 and about 9.

24. The method of claim 21 wherein the pH of said mixture is about 6.

25. The method of claim 21 wherein said mixture is applied post harvest.

26. The method of claim 21 wherein said mixture is applied at a temperature of between about 45° F. and about 150° F.

27. The method of claim 21 wherein said mixture is applied at a temperature of about 50° F.

28. The method of claim 21 wherein said mixture is applied at a temperature of about 75° F.

29. The method of claim 21 wherein said mixture is applied at an ambient temperature.

30. The method of claim 21 wherein said mixture is sprayed onto crop in a field having night temperatures of between about 0° C. and about 10° C., and day temperatures of between about 10° C. and about 25° C.

31. The method of claim 21 wherein said mixture is sprayed onto crop in a field having an ambient temperature range of between about 10° C. and about 30° C.

32. The method of claim 21 wherein the pH of said mixture is between about 3 and about 9.

* * * * *